US006429926B1

United States Patent
Williamson et al.

(10) Patent No.: US 6,429,926 B1
(45) Date of Patent: Aug. 6, 2002

(54) OPTICAL FLOW METER CAPABLE OF OPERATING WITH A VARIABLE REFRACTIVE INDEX

(75) Inventors: Ian D. Williamson, Ottawa (CA); Sergei A. Sharonov; Pierre-Jean Daniel, both of Houston, TX (US); Darwin E. Kiel, Burnaby (CA)

(73) Assignee: Nova Gas Transmission Ltd., Calgary (CA)

( * ) Notice: Subject to any disclaimer, the term of this patent is extended or adjusted under 35 U.S.C. 154(b) by 0 days.

(21) Appl. No.: 09/756,405

(22) Filed: Jan. 8, 2001

(51) Int. Cl.[7] .............................. G01P 3/36; G01F 1/00
(52) U.S. Cl. ........................ 356/28; 356/28.5; 73/861
(58) Field of Search ................................ 356/277, 28.5; 73/861

(56) References Cited

U.S. PATENT DOCUMENTS

| | | | | |
|---|---|---|---|---|
| 4,201,467 A | * | 5/1980 | Hartmann et al. | 356/28 |
| 4,664,513 A | * | 5/1987 | Webb et al. | 356/28 |
| 4,707,130 A | * | 11/1987 | Hofmann et al. | 356/28 |
| 4,789,215 A | * | 12/1988 | Anderson | 350/96.19 |
| 4,804,263 A | * | 2/1989 | Schodl | 356/28 |
| 4,851,697 A | * | 7/1989 | Schodl | 250/574 |
| 4,978,863 A | * | 12/1990 | Lyons et al. | 356/28 |
| 5,000,566 A | * | 3/1991 | Kuppenheimer, Jr. et al. | 356/28 |
| 5,131,741 A | * | 7/1992 | Zweben | 356/28 |
| 5,148,229 A | * | 9/1992 | Wiseall | 356/28 |
| 5,268,739 A | * | 12/1993 | Martinelli et al. | 356/349 |
| 5,365,326 A | * | 11/1994 | Chrisman et al. | 356/28.5 |
| 5,701,172 A | * | 12/1997 | Azzazy | 356/28 |
| 5,865,871 A | * | 2/1999 | Simundich | 73/861 |
| 6,128,072 A | * | 10/2000 | Kiel et al. | 356/28 |
| 6,137,116 A | * | 10/2000 | Amir et al. | 250/559.44 |

OTHER PUBLICATIONS

High Speed Nozzle Flowmeter Using Miniaturized Laser–Doppler Techniques; Mar. 20–22, 1995; V. Stunck, E.–A. Krey,, H. Müller and D. Dopheide; Braunschweig Germany.
Laser Velocimetry; Jun. 10–14, 1991; M.L. Riethmuller; Genese–Belgium.

* cited by examiner

Primary Examiner—Thomas H. Tarcza
Assistant Examiner—Brian Andrea
(74) Attorney, Agent, or Firm—Conley, Rose & Tayon, PC (57) ABSTRACT

An optical design for delivering or receiving light from a fluid being measured is disclosed. The optical design is capable of immersion in the fluid being measured, and is capable of operating with fluids that have a different index of refraction. The optical design includes a solid prism of optical material to which a fiber optic attaches by a suitable adhesive. In an optical delivery system, light from the fiber enters the prism and reflects off an internal mirror to a second internal reflective surface. The second internal reflective surface focuses the light to a fixed point through an exit surface of the prism. The second internal reflective surface may in the shape of an ellipse, or may comprise a diffractive surface. The exit surface has a spherical concave shape that is centered on the fixed point where the light is focused, so that light passes through the exit surface at substantially ninety degrees. In an optical collection system, light from a point enters the prism at an entry surface, that is spherically concave so that light passes through the entry surface at substantially ninety degrees. Light then reflects from a first internal reflective surface that may be a diffractive lens or an elliptically shaped lens, to thereby focus the light received from the point. Light reflecting from the first internal reflective surface is received at a second mirrored surface, where the light is reflected to the base of the prism, where the fiber optic attaches.

58 Claims, 3 Drawing Sheets

OPTICAL FLOW METER CAPABLE OF OPERATING WITH A VARIABLE REFRACTIVE INDEX

CROSS-REFERENCE TO RELATED APPLICATIONS

This application relates to U.S. application Ser. No. 09/065,364, entitled "Optical Flow Meter Integrally Mounted to a Rigid Plate With Direct Optical Access to the Interior of a Pipe," and to U.S. application Ser. No. 09/526,326, entitled "Pipeline Optical Flow Meter," both of which are incorporated by reference as if fully set forth herein.

STATEMENT REGARDING FEDERALLY SPONSORED RESEARCH OR DEVELOPMENT

Not applicable.

BACKGROUND OF THE INVENTION

1. Field of the Invention

The present invention generally relates to optical flow meters for measuring flow characteristics of a fluid in a pipe. More particularly, the present invention relates to an optical flow meter in which at least part of the optical flow meter mounts within the pressurized environment of the pipe. Still more particularly, the present invention relates to optical systems that are used to focus and collect light beams inside a pressurized pipe, and which are subjected to the fluid within the pipe.

2. Background of the Invention

In pipeline operations and other industrial applications, flow meters are used to measure the flow rate of gases or liquids moving through the pipeline or tubing system. In natural gas pipelines, for example, these flow rate measurements are used for custody transfer, leak detection, control, or for other purposes. Custodial transfers of hydrocarbons and other fluids require very accurate measurements of the fluid being transferred. The flow meter typically is used as the transfer point for a custody transfer to determine the amount of fluid that has been transferred. By accurately measuring the flow rate for a particular transfer period, the volume of liquid that flows through the pipeline can be determined, and a custody transfer volume ticket can then be prepared. The pipeline transportation fee is based on the volume of product moved through the system, i.e. the custody transfer volume. Thus, a custody transfer metering system is commonly referred to in the pipeline industry as the "cash register," and pipeline operators take great care to maintain its measurement accuracy.

Various meters have been used to measure the flow of liquids in pipelines and other tubing systems. Existing meters can be separated into three general categories for purposes of discussion. The first type of meters is obstruction meters. Obstruction meters determine fluid flow rates by introducing a physical obstruction directly into the flow of fluid, and measuring the influence of the fluid on the obstruction. One type of obstruction meter is those that introduce a flow restriction in the pipeline, such as a reduced-diameter orifice plate. The flow restriction creates a pressure drop, which can be measured and used to calculate the fluid flow rate through the restriction. In addition to orifice meters, venturi meters and critical flow nozzles also make use of flow restrictions to measure fluid flow rates. Other obstruction meters include vortex meters.

Obstruction meters have the inherent disadvantage of extracting energy from the fluid flow as a consequence of the pressure drop. The inefficiencies caused by the physical obstruction require additional pumping capacity to overcome. In addition, the physical obstruction also acts as an impediment to using pipeline pigs or other devices that scrub the interior of the pipeline. In addition, because the obstruction-type meter is placed directly in the fluid flow, the meter components may be subject to premature wear, requiring maintenance and replacement. These meters also are characterized by low turndown ratios (i.e. a limited range of flow rates for which accurate measurements are possible) due to the non-linear relationship between flow rate and pressure drop.

The second type of flow meter is kinematic meters. Kinematic meters determine the flow rate by directly sensing the actual velocity of the fluid using a turbine blade assembly that rotates kinematically with the flow. The rotational speed of the turbine is measured using a frequency transducer, and then is empirically related to flow rate using an experimentally determined coefficient. Kinematic meters provide an output that is approximately proportional to volumetric flow rate and substantially independent of density. The primary disadvantage of kinematic meters is the presence of moving parts, the obstruction to the fluid flow, the requirement of electrical power, and the physical size of the meter.

The third class of flow meters are those that use non-intrusive methods to determine flow rate. The ultrasonic meter is the only meter in this category that has been commercially developed for use in high pressure natural gas pipelines. An ultrasonic meter compares the upstream and downstream transit times of an acoustic pulse from transducers located near the inside surface of the pipe. The fluid flow therefore is unrestricted, and thus these meters do not produce any significant pressure drop. These devices, however, require a relatively long installation length (on the order of a few pipe diameters), are limited to larger pipe sizes, and can suffer from acoustic noise in the vicinity of the meter.

As noted in U.S. application Ser. No. 09/065,364, entitled "Optical Flow Meter Integrally Mounted to a Rigid Plate With Direct Optical Access to the Interior of a Pipe," incorporated by reference herein, optical flow meters are non-intrusive flow meters that potentially overcome many of the disadvantages that exist with existing commercial flow meters, if the optical flow meter can be designed in a sufficiently compact space, with adequate access to the pipe interior.

Flow rates may be determined with optical meters by measuring the velocity of particles suspended in a representative field in the fluid flow. The particles preferably are under 100 microns in diameter, and more preferably under 25 microns in diameter. The velocity is measured by determining the time-of-flight of these particles as they move between two discrete regions that have been illuminated with light from a laser. See e.g. D. H. Thomson, "A Tracer Particle Fluid Velocity Meter Incorporating a Laser," Jour. Of Sci. Inst. (J. Phys. E.) Series 2, Vol. 1, 929–932 (1968). The time-of-flight concept has been applied to measure the air speed of an aircraft, as described in U.S. Pat. Nos. 4,887,213, 5,046,840 and 5,313,263.

Optical techniques also have been used by numerous investigators to make measurements in laboratory environments, such as wind-tunnels and turbo machinery. See R. Schodl, "A Laser-Two-Focuse (L2F) Velocimeter for Automatic Flow Vector Measurement in Rotating Components of Turbomachines," Transaction of the ASME, Vol.

102, p. 412 (December 1980). Additionally, UK Patent 2,295,670 describes a configuration in which laser light from an argon ion laser is split by a Rochon prism, made parallel by a lens and then focused into two spots. Scattered light produced by particles passing through the two spots is imaged onto two photoelectric converters. Velocity is determined on the basis of the transit time of the particles passing between the two spots. U.S. Pat. No. 4,125,778 discloses a similar device, except that the relative position of the two spots can be rotated using an optical component. A variation on the time-of-flight principle using individually addressable laser diode arrays was described in U.S. Pat. No. 5,701,172 to measure the velocity profile inside a high pressure natural gas pipeline through a glass window. The image of the diode array produces a series of spots in space and the light scattered by small particles is collected and converted to electrical signals. The frequency content of the signal and the spacing of the spots of light are used to determine the flow velocity. Alternatively, the patent describes the system in combination with a holographic lens placed as a window in the pipeline wall, thereby permitting multiple measurement locations along one pipe diameter. However, the requirement of a relatively large glass window in the pipeline renders this design impractical for broad commercial applications because of cost and safety concerns.

Related U.S. application Ser. No. 09/065,364, entitled "Optical Flow Meter Integrally Mounted to a Rigid Plate With Direct Optical Access to the Interior of a Pipe," describes an optical flow meter in which the optical components are mounted in a rigid plate that is placed within the pressurized pipe environment. According to the preferred embodiment, the plate fits within a conventional pressurized orifice meter in place of a convention plate carrier. This enables the optical components to have direct access to the fluid flow, without requiring use of a glass window in the pipeline. Because the optical components are mounted in the wall of the orifice plate, the meter does not produce any significant pressure drop in the passing fluid.

Thus, in the field of optical flow metering, there is a need to focus light to a point in space within a pressurized pipe and to collect the light scattered by particles in the fluid. The signal generated by one or more photo detectors then can be used to determine the velocity of the fluid in several ways, including Laser Doppler Anemometry (LDA) and time of flight anemometry. The optical meter typically is calibrated in air under laboratory conditions, prior to being used in a natural gas, or other measuring environment. The problem, however, is that the refractive index of air differs from the refractive index of the fluid being measured, thus compromising the integrity of the subsequent measurement when the meter is placed in the field. Put simply, the characteristics of the multiple light paths, which are used for the flow measurement, will vary depending on the medium in which the optics are placed. If the optical system measures velocity based on the transit times of particles between two beams, and the beams are displaced because of a differing refraction index, then the velocity measurement will be compromised. Additionally the performance of optics used to collect scattered light can be adversely affected. In particular, applications in pressurized gases pose significant difficulties, because the refractive index of the gas changes with pressure, temperature, and composition. Natural gas, for example, has an index of refraction that may vary from approximately 1.00 at atmospheric conditions to 1.04 at pressures encountered in high pressure pipelines. Such a variation in the index of refraction can cause significant degradation in the performance of conventional optical systems, to the point that they may no longer be functional.

One technique for overcoming the difficulties with refractive index variation were disclosed in U.S. patent application Ser. No. 09/065,364. In that disclosure, the use of quarter pitch gradient index (GRIN) lenses for collimation was suggested. For optical components in which larger apertures and faster (low f numbers) lenses are needed, a novel lens design was disclosed. This lens included (i) two or more elements that had very large differences in refractive index, such as $CaF_2$ and $ZnS$; (ii) first and last surfaces that were concave and defined by spherical surfaces centered at the object and image locations, respectively; and (iii) cemented internal surfaces between the elements shaped in such a way as to provide all the focusing power necessary to image the object at the desired location. The use of spherical surfaces centered at the object and image locations ensures that the light enters and exits the lens perpendicular to the local surface, and therefore is not affected by the index of refraction of the fluid in contact with the lens faces.

While the optical meter disclosed in U.S. patent application Ser. No. 09/065,364 overcomes many of the problems with prior optical flow meters, the preferred embodiment disclosed therein requires multiple optical components that are subject to premature wear and contamination, as particles in the fluid may become entrapped between optical components. The image and object locations are fixed, and thus so is the light path used to measure flow rate. If the fluid contains particles, a significant portion of the light may be blocked by contaminants on optical surfaces in line with object or image locations. For example, if the end of an optical fiber is either the light source to be focused to a point in space, or the image location for light collected from a point in space, a small amount of dirt on the end surface of the fiber may very seriously degrade the performance of the system.

An alternative design that has been used in industry is a probe in which the optics are contained within a sealed package with low pressure gas (such as air) between the optical components and the window. Examples of probe designs may be found in U.S. Pat. Nos. 5,365,326 and 4,978,863. In addition, TSI manufactures a probe that includes optical components mounted in a sealed probe, with a window that permits light beams to be transmitted and received by the optical components inside the probe. The use of the sealed housing in these designs makes it possible to keep most of the optical surfaces clean. These probes generally have flat optical surfaces in contact with the fluid and hence are sensitive to the index of refraction of the surrounding fluid. This design, however, has some severe limitations, especially in the context of high pressure gases. When such an assembly is left in a high pressure gas environment, it is extremely difficult to prevent leakage of the gas into the sealed housing. Unless extreme precautions are taken the gas will tend to leak into the unit through the seals, either due to defects in the sealing materials, or through molecular diffusion. This leakage may degrade optical performance due to the differing refractive index of the air and the gas. An even more critical problem, however, may result when the probe is removed from the high pressure gas for inspection, servicing or replacement. Once the probe is removed, the internal pressure significantly exceeds atmospheric pressure, and the pressurized gas in the internal volume of the probe in effect makes the assembly a bomb that could explode at any time, thereby posing a significant risk to workers. Techniques to minimize this problem would be to fill the probe with a liquid or gel that would minimize gas leakage into the chamber. Such a design, however, raises problems in terms of gas solubility in the gel or liquid, and problems with optical performance due to a reduced difference in refractive index between the lenses and the cavities within the assembly.

It would be desirable if an optical flow meter could be designed that significantly reduces the problems caused by subjecting the meter to different flow mediums with a different index of refraction. It would also be desirable to develop an optical design that can be immersed in the fluid being measured, without creating unsafe pressure build-ups. In addition, it would be desirable if the optical components could be integrated in a package that would significantly reduce the problems caused by contaminants within the optical system. Despite the apparent advantages of such a system, to date no such system has been developed.

BRIEF SUMMARY OF THE INVENTION

The present invention solves the deficiencies of the prior art by incorporating a very compact optical system design in an optical flow meter. The compact optical system design avoids problems with contamination of the image or light source location by integrating the optical delivery system into a single integrated package, with no internal cavities. According to the preferred embodiment, one or more optical fibers is attached to the optical system to avoid interference by particles in the fluid being measured. The optical design preferably comprises a pentaprism design that includes two internal mirrored surfaces. According to one embodiment, a concave spherical surface is used as the surface closest to the image. The concave spherical surface is centered at the image location to ensure that the light enters and exits the lens perpendicular to the local surface, and therefore is not affected by the index of refraction of the fluid in contact with the lens faces.

According to the preferred embodiment, the present invention relates to an optical flow meter that generates a signal containing information that may be used to describe fluid flow within a pipeline, based on the motion of particles suspended in the fluid. The flow meter preferably includes a narrow frequency light source and one or more fiber optic cables that transmit light from the light source to an optical delivery system disposed within the pressurized environment of the pipe. The optical delivery system preferably collimates and focuses two light beams into two parallel planes within the fluid flow. Alternatively, a Laser Doppler Velocimetry (LDV) optical system may be used to focus multiple light beams to a point within the pipeline. Light scattered by particles in the fluid is collected by an optical collector, which collects the light and transfers the light via one or more fiber optic cables to a light detector. The light detector converts the light pulses into electrical signals that are analyzed by a computer or signal processing device.

According to one embodiment of the present invention, a pentaprism design may be used as either the optical delivery system, or as the collector, or as both the optical delivery system and collector simultaneously, in an optical flow meter. The collector pentaprism design includes a concave surface that receives the scattered light from the image. The concave surface is designed as a spherical surface centered at the image. Consequently, light passes from the image perpendicularly through the concave spherical surface. The light passing through the concave spherical surface reflects off a mirrored surface that preferably has an elliptical shape. Light from the elliptical mirrored surface reflects off a flat mirrored surface that focuses light into a fiber optic cable that is firmly attached to base of the pentaprism.

According to another embodiment of the invention, the optical delivery system pentaprism design has a generally flat base surface, to which a fiber optic cable is firmly attached. The fiber optic cable carries light from the light source. Light from the end of the fiber optic cable reflects off a flat mirrored surface located opposite the flat base surface. Light from the flat mirrored surface strikes a side wall of the prism. This wall may be configured as an elliptical mirror, but preferably comprises a diffractive lens element. Light reflects off the diffractive element and is focused on the image. Between the diffractive lens element and image is the opposite side wall, which may comprise a concave spherical exit surface. To produce a pair of light beams, two pentaprisms may be effectively stacked together in a single integrated package. This may be done by stacking two diffractive elements on the side wall of the pentaprism to insure the two light beams are in parallel.

Additional details of the present invention will become apparent by studying the following Detailed Description of the Preferred Embodiment.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical or optical connection. Thus, if a first device couples to a second device, that connection may be through a direct connection, or through an indirect connection via other devices and connections. The term "fluid" is used in its customary sense to encompass both liquids and gases. To the extent that any term is not specially defined in this specification, the intent is that the term is to be given its plain and ordinary meaning.

DETAILED DESCRIPTION OF THE PREFERRED EMBODIMENTS

The optical flow meter constructed in accordance with the preferred embodiment determines the flow rate of fluid within a pressurized pipe. According to the preferred embodiment, the optical flow meter integrally mounts in a rigid plate, such as a customized orifice plate, that is inserted into a conventional orifice meter. It should be understood, however, that the optical flow meter of the present invention may be incorporated into other structures to permit direct access to the pipe interior, without using an orifice fitting. Thus, for example and without limitation, the optical flow meter of the present invention may be installed in the pipeline between the flanges of two adjacent pipe sections.

Figure 1:
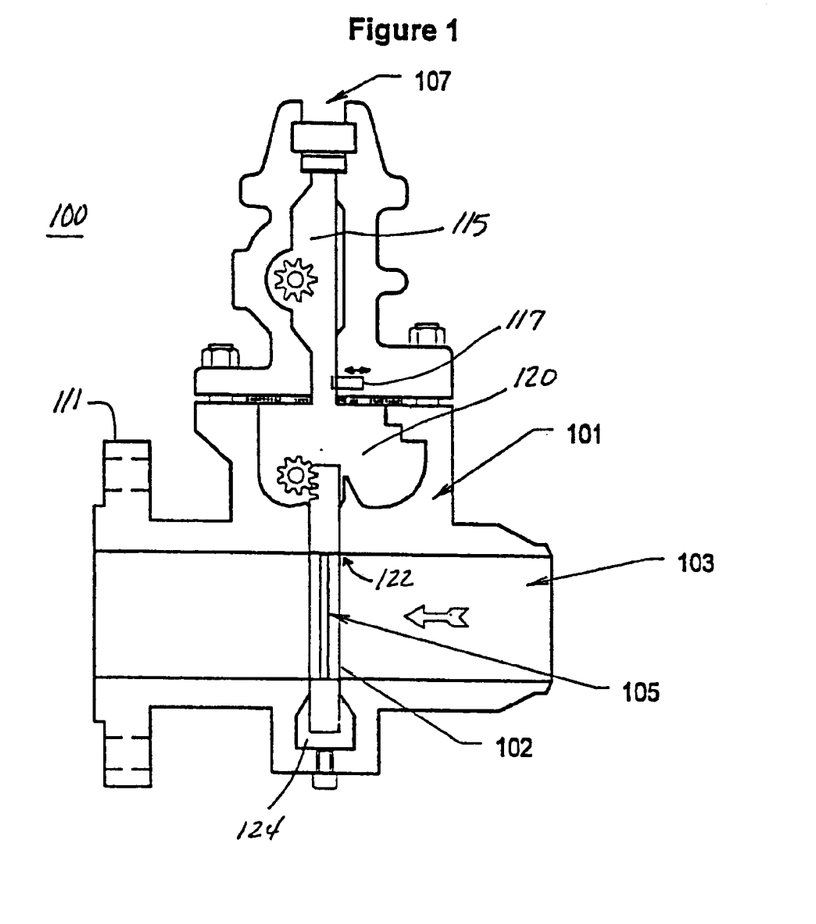
FIG. 1 is a schematic illustration of an orifice meter constructed in accordance with the preferred embodiment.

Referring initially to FIG. 1, an orifice meter 100 typically comprises a cylindrical bore 103 and meter body 101. The cylindrical bore typically terminates in a flange 111 on each end of the cylindrical bore 103, to which a section of tubing attaches (only one such flange is shown in FIG. 1). Thus, the cylindrical bore 103 functions as a section of pipeline through which fluid flows for analysis by the orifice meter. Preferably, the cylindrical bore has the same internal diameter as the adjacent pipe sections, so that no pressure drop is induced by the orifice meter 100. The cylindrical bore 103 includes an upper opening 122, typically in the vicinity of its midpoint, that operates as a conduit permitting access to the interior of the cylindrical bore 103 from the meter body 101. The cylindrical bore 103 also includes a lower recess 124 that receives and retains a carrier plate 102 when it has been fully inserted in the orifice meter 100.

The orifice body 101 includes a closable opening 107 at its upper end that provides access to cavities within the orifice body. According to one conventional meter design, the orifice body includes an upper cavity 115 and a lower cavity 120, which are separated by a slide valve 117, thereby permitting the carrier plate 102, containing the orifice plate 105, to be inserted in the cylindrical bore 103 of the orifice meter 100 while pressurized fluid flows through the cylindrical bore 103. During installation, the slide valve 117 is closed and the closable opening 107 is opened to provide access to the upper cavity 115. The carrier plate 102 then is inserted into the upper cavity 115. Once the plate 102 is fully inserted into the upper cavity 115, the closable opening 107 is shut, and the slide valve 117 is opened. The plate 102 is then transported into the lower cavity 120, and inserted through the conduit 122 into the interior of the cylindrical bore 103. The slide valve 117 is closed when the plate 102 has been inserted into the cylindrical bore 103. When the carrier plate 102 is removed, the same steps are used, in the reverse order.

As one skilled in the art will understand, the fluid flowing through the cylindrical bore passes into the lower cavity 120, and when the slide valve 117 opens, also passes into the upper cavity 115. The two step insertion (and removal) process minimizes the amount of fluid that escapes out of the pipeline, while safely maintaining the pressure within the pipeline. The pressurized fluid fills the lower recess 124. Thus, when the carrier plate 102 is inserted into the flow stream of the pressurized fluid, the carrier plate 102 is within the pressurized environment of the pipe, and typically is immersed in the fluid flowing through the pipe.

Prior art orifice plate designs typically mount within a plate carrier, and have a central hole that has a smaller diameter than the bore, thus introducing a pressure differential. According to the preferred embodiment of the present invention, the carrier plate 102 differs from conventional designs in that it comprises a single rigid plate, although the plate could be used in conjunction with a separate carrier. In addition, unlike conventional orifice plates, the carrier plate implemented in the preferred embodiment includes a central aperture 105 that has approximately the same dimensions as the interior of the cylindrical bore 103, which in turn has the same dimensions as the adjoining pipe sections. Thus, the orifice meter 100 and carrier plate 102 are designed to minimize pressure drops or differentials in the pressurized fluid.

Figure 2:
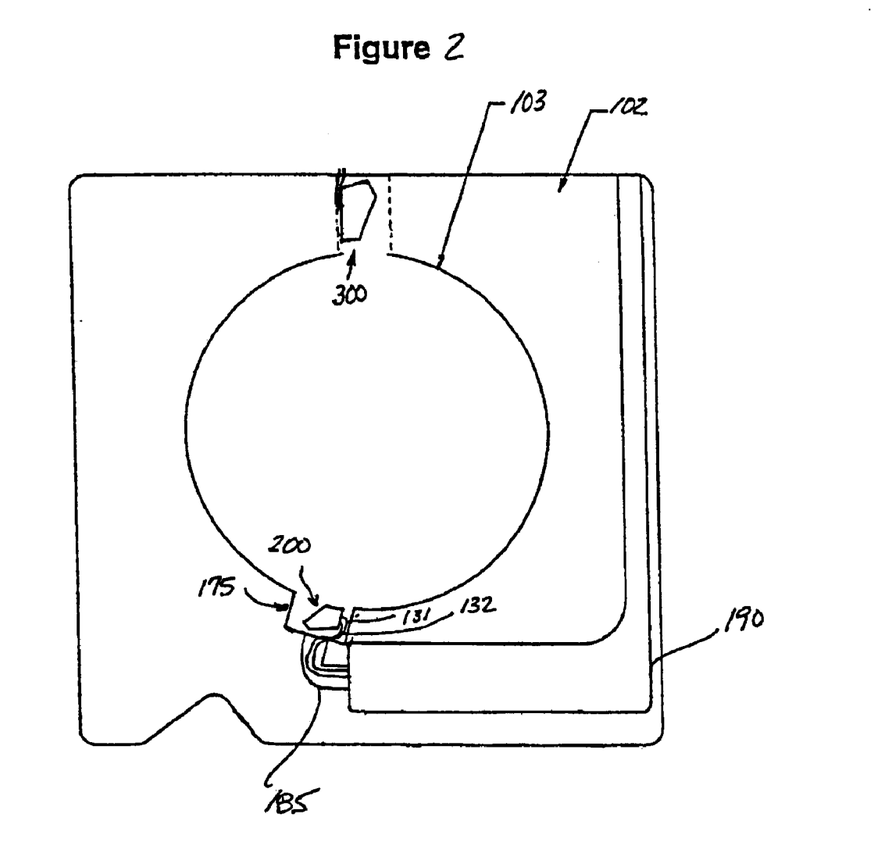
FIG. 2 shows a plate, which installs in place of a conventional "plate carrier" in the orifice meter of FIG. 1, constructed in accordance with the preferred embodiment with an optical delivery system and collector lens mounted in cavities therein.

Referring now to FIG. 2, the carrier plate 102 supports at least one optical delivery system 200 that preferably provides at least two light beams focused within the fluid flow. More than one optical delivery system may be implemented if desired, and more than two light beams may be used. The carrier plate 102 also preferably holds a collector system 300 that receives light scattered from particles in the fluid. In accordance with the preferred embodiment, the optical delivery system provides a pair of parallel light beams, separated by a known distance. The two light beams are preferably oriented perpendicularly to the longitudinal axis of the pipe, with one light beam located upstream of the other (relative to the flow stream). Additional details regarding the placement of the beams and the operation of the meter may be obtained from U.S. patent application Ser. No. 09/065,364, which has been incorporated by reference herein. Alternatively, the light beams may be configured to intersect each other using a Laser Doppler Velocimetry ("LDV") technique.

As shown in FIG. 2, the optical delivery system 200 preferably mounts within a recess 175 in the inner wall of the carrier plate. According to the preferred embodiment, the recess 175 is configured to accommodate the optical delivery system 200 so that the optical delivery system is positioned in the recess and does not protrude into the bore region 103. While the optical delivery system forms a portion of the cylindrical bore wall, in the preferred embodiment no attempt is made to seal the optical delivery system from the fluid. Thus, according to the preferred embodiment, the fluid flowing through the cylindrical bore under pressure may leak behind and around the optical delivery system. As a result, considerable cost savings result since there is no requirement that the high pressure fluid be sealed within the cylindrical borehole. In addition, the absence of seals reduces the possibility of pressure differentials in the flowing medium. Two fiber optic cables 131, 132 preferably attach to the base of the optical delivery system 200 with a suitable epoxy, or through an optical waveguide device. The fiber optics extend through channels 185 machined in the carrier plate 102. Preferably, a plate 190 attaches over the channels to secure the fiber optics within the channel, and to facilitate handling without disturbing the alignment of the fiber optics. When the carrier plate 102 is filly inserted within the orifice meter 100, the fiber optics 131, 132 extend from the channel on the upper side of the carrier plate, and pass through the upper and lower cavity regions 115, 120 in the meter body (FIG. 1). The fiber optics pass out of the meter body via a pressure fitting located in the closable opening 107 of FIG. 1. Other pressure fittings may also be provided in other valves, as required.

Figure 3:
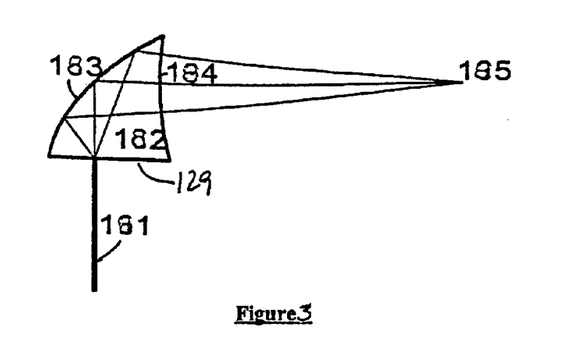
FIG. 3 shows a compact right angle prism that may be used in accordance with one embodiment of the invention as the optical delivery system or collector lens.

Referring now to FIG. 3, the optical components of the present invention provide for either the delivery of light to a point in space or the collection of light from a point in space back to a focal point. For the purposes of the following description, the delivery of light within the cylindrical bore case will be described, with the understanding that the same principles apply in reverse to the collection of the scattered light.

Figure 4:
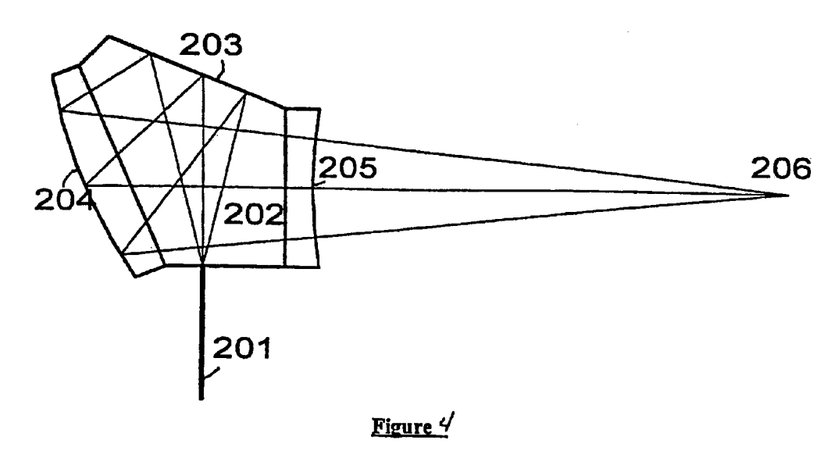
FIG. 4 shows a pentaprism design that is used in accordance with the preferred embodiment as the collector lens.
Figure 5:
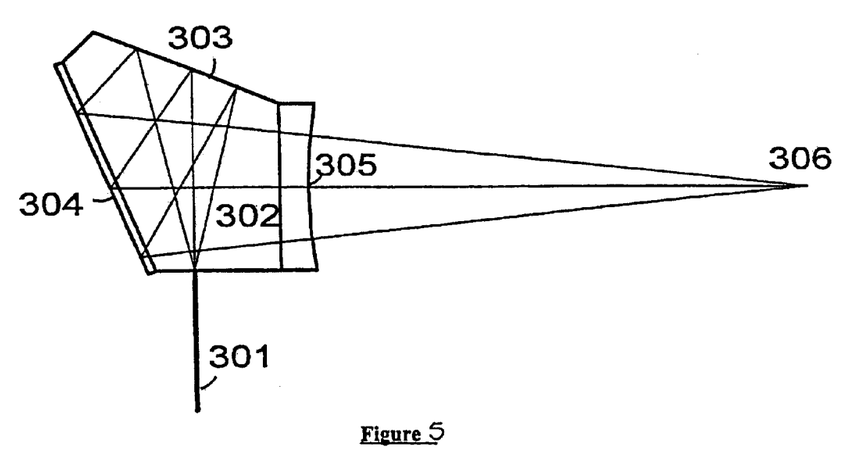
FIG. 5 shows a pentaprism design that is used in accordance with the preferred embodiment as the optical delivery system.

According to the preferred embodiment, the optical components are configured to eliminate contaminants in the optical path, while achieving a compact design. In that regard, the optical delivery system (and similarly, the collection system) preferably define an optical path that, to the extent possible, is contained inside solid glass or some similar optical material. Thus, as compared to the optical delivery system in U.S. patent application Ser. No. 09/065,364, the optical path is largely contained within glass. In U.S. patent application Ser. No. 09/065,364, the optical delivery system includes a collimator, beam splitting prism, mirror and focusing lens, that are separately located in the optical path. Thus, particles in the pressurized fluid may block the light path between these various optical components. By enclosing the optical path within glass in accordance with the preferred embodiment of the present invention, problems with contaminants becoming entrapped between optical components can be largely eliminated. In addition, placing the optical path within glass or other optical materials reduces the possibility of high pressure gas becoming trapped by optical components, which may result in a safety hazard. Similarly, according to the preferred embodiment, light is focused using internal mirrors in the solid glass, which may be either conventional curved mirrors, or diffractive mirrors. To further reduce the possibility of contaminants interfering with the optical path, the light source (or one or more fiber optic cables coupling the light source to the optical delivery system) preferably is placed in contact with a face of the solid optical delivery system. According to the preferred embodiment, a prism is used as the optical delivery system, and thus the light source or fiber optic is placed in contact with the face of the prism, thus preventing contaminants from becoming lodged between the source and the optical delivery system. Finally, the last surface of the prism (where the light leaves the solid optical material) preferably has a concave configuration so that the light leaves the last surface substantially perpendicular to the prism material. If the light is to be collimated, or very nearly collimated, the surface could be flat. This configuration of the exit surface insures that the optical delivery system will not be adversely affected when subjected to fluids that have a different index of refraction. Three basic designs for implementing these principles are shown in FIGS. 3, 4 and 5, which will be discussed below. It will be apparent to one skilled in the art that other designs also may be used to implement an optical design according to these design parameters.

In its simplest form, the basic optical design of FIG. 3 may be used as the optical delivery system and/or the optical collection system. The optical design of FIG. 3 includes a fiber optic 181 coupled to a right angle prism 182. The right angle prism 182 preferably includes a flat base 129, an elliptical surface 183, and a concave spherical surface 184. Light leaving the fiber 181 enters through the base 129 and reflects off elliptical surface 183, where it is focused to point 185. The exit surface 184 preferably comprises a spherical surface centered at point 185, thus insuring that light focused on point 185 passes from the elliptical surface to the point 185 at substantially ninety degrees through the concave exit surface. This exit angle substantially eliminates problems that may otherwise result if fluids with a different refractive index are metered with the same optical components. The fiber optic and prism preferably are bonded using optical adhesive, such as a UV-curing adhesive commonly used in optical lens fabrication. As one skilled in the art will appreciate, the prism may be constructed of a number of sub components that individually may be easier to fabricate, but which are cemented together to produce prism 182. Alternatively, prism 182 may be constructed by molding or machining a piece of optical material, such as glass, to reduce the number of parts that would be required. Additional elements to support the fiber and provide strain relief would generally be beneficial.

Referring now to FIGS. 4 and 5, the optical delivery system and optical collection system preferably are constructed based on a pentaprism. According to normal convention and as shown in FIG. 4, the pentaprism typically has five sides. However, it should be noted that the shortest of the five sides of a typical pentaprism often has no optical function and may be eliminated by extending the two adjacent sides until they intersect. Designs based on a pentaprism may also include additional sides (in excess of five), as shown for example in the exemplary designs of FIGS. 4 and 5, due to the manufacture of the prism from separately made parts. It should also be understood that although a pentaprism is used in the preferred embodiment, other prisms or optical designs may be used, as indicated by the optical design depicted in FIG. 3. The pentaprism provides for a more compact design, while allowing a longer optical path between the fiber optic (or fiber optics) and the focusing surface, which in turn makes certain conjugate ratio optical systems more practical. Pentaprisms also offer reflection angles that are much closer to perpendicular and are therefore especially advantageous for diffractive lenses which suffer losses of efficiency with shallow angles of incidence and reflection. An additional advantage of the pentaprism is that the light received by the prism is focused into the fiber at an angle that is closer to perpendicular. This is advantageous because every fiber has a limiting angle outside of which light cannot be received into the core of the fiber. This limiting angle is conventionally described by a "numerical aperture" or "NA", which is defined by the sin of the half angle of the cone. With reference to FIG. 3, it is evident that light emitted from point 185 at some angle above the optical axis, is collected by the prism and focused into the fiber at another angle. By comparison, light emitted from point 185, but at the same angle below the optical axis, enters the fiber at an angle that is farther from perpendicular.

Two alternative embodiments employing curved and diffractive mirrors and pentaprisms are illustrated in the cross sections in FIGS. 4 and 5, respectively. The design of FIG. 5 is preferred for use as the optical delivery device, which the design of FIG. 4 is preferred as the collection lens. It should be understood, however, that either design (or other similar designs) may be used as the optical delivery prism or the collection prism, or as both the delivery and collection prism simultaneously. In FIG. 4, light emitting from the optical fiber 201, which is cemented to the pentaprism 202, travels to a flat mirrored surface 203 and reflects from mirrored surface 203 toward mirrored surface 204. Mirrored surface 204 preferably is defined by a surface resulting from the rotation of an ellipse about its major axis. The light leaving elliptical mirrored surface 204 converges toward the focal point 206, preferably passing perpendicularly through the concave spherical surface 205. If appropriate for the conjugate ratio of the optical design required, the first mirrored surface 203 could be curved, and the second mirrored surface 204 could be flat. In practice, the elliptical surface can be constructed as part of a separate element and cemented to the prism if desired for simplifying the manufacture of the optical system. Similarly, the spherical concave surface 205 can be produced as part of a plano-concave element and cemented in place. Such an arrangement is depicted in FIG. 4, with separate plano-elliptical and plano-spherical elements cemented to the prism.

FIG. 5 shows a system similar to FIG. 4, except that a diffractive element is used instead of the elliptical mirrored surface. In FIG. 5, light emitting from the optical fiber 301, which is cemented to the pentaprism 302, travels to a mirrored surface 303. Light reflects from the mirrored surface 303 toward a diffractive mirrored surface 304, which causes the light leaving surface 304 to converge toward the focal point 306, preferably passing perpendicularly through the concave spherical surface 305. If appropriate for the conjugate ratio of the optical design required, the first mirrored surface 303 could be diffractive, and the second mirrored surface 304 could be flat. In practice, the mirrored diffractive element can be make on a thin substrate and cemented to the prism to simplify the manufacturing. Similarly, the spherical concave surface 305 can be produced as part of a plano-concave element and cemented in place. FIG. 5 depicts these optical components as separate parts cemented to the prism. In general, both reflected surfaces in the pentaprism may have optical power (e.g. curvature) if this is advantageous for a particular application. The disadvantage of such an arrangement is the increased complexity of manufacture, but that disadvantage may be outweighed by the optical advantages that such a design presents in a particular application.

It should be noted that the devices described in FIGS. 4 and 5 also work in reverse; that is, they also may receive light emitted from a point in space and focus it to a point located at the end of the fiber optic. In the disclosure above, the light sources and light receivers which are coupled to the prism have generally been referred to as fibers, however the sources could be laser diodes or LED's and the receivers could be photo-detectors with suitable protection from the surrounding fluid.

The above disclosure discusses an optical component that produces a single light beam. Multiple light beams may be produced by stacking similar optical components on each other. Thus, for example, two pentaprism designs constructed in accordance with the teachings of FIG. 4 (or FIG. 5), may be stacked one on the other to generate two parallel or intersecting beams within the interior of the pipeline. Similarly, two pentaprism designs may be stacked one on the other to collected light scattered by particles in the fluid. As one skilled in the art will understand, this stacking can be implemented in integral fashion in a single prism to maintain the compactness of the design. In practice, the stacked optical design would then include a fiber optic for each stacked optical component. Thus, if two optical delivery systems were integrally stacked, two fiber optic cables would attach, with one optic cable associated with each delivery system The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An optical assembly that focuses light to a point in space within a light transparent fluid of any refractive index, comprising:
   a light source;
   a prism coupled to said light source, said prism passing light from said light source to the point within said fluid through a single optical exit surface; and
   wherein the optical exit surface of said prism is configured as a spherical surface centered at said point, and wherein the optical path from said light source to said exit surface substantially comprises only solid optical materials.

2. An optical assembly as in claim 1, wherein said light source couples to said prism via an optical fiber, and said optical fiber attaches to a first surface of said prism.

3. An optical assembly as in claim 1, wherein said prism further comprises a first base surface to which said light source couples, and a first internal reflective surface that reflects light.

4. An optical assembly as in claim 3, wherein said prism includes an internal mirror that receives light from said first internal reflective surface and focuses light to said point in said fluid.

5. An optical assembly as in claim 4, wherein said internal mirror is formed by rotation of an ellipse about its major axis.

6. An optical assembly as in claim 4, wherein said internal mirror is a fabricated diffractive surface.

7. An optical assembly as in claim 1, wherein said prism comprises a right angle prism.

8. An optical assembly as in claim 1, wherein said prism comprises a pentaprism.

9. An optical assembly as in claim 8, wherein said pentaprism has 3 adjacent internal angles measuring, in order, 112.5°, 90°, and 112.5°.

10. An optical assembly as in claim 1, wherein at least two prisms are used in combination to measure the velocity of fluid flowing through a pipeline.

11. An optical assembly as in claim 1, wherein said optical assembly is immersed in said fluid.

12. An optical assembly as in claim 11, wherein said fluid includes natural gas that flows through a pressurized pipeline.

13. An optical assembly as in claim 1, wherein said light source comprises an array of sources which are sufficiently closely spaced so that the light enters the optical material at a substantially perpendicular angle and said point remains substantially fixed as the refractive index of the medium changes.

14. An optical assembly as in claim 1, wherein said fluid is natural gas.

15. An optical assembly that measures fluid flowing through a pipeline, comprising:
    a light source that produces light focused at a point in the fluid;
    a prism located in the fluid that collects light scattered from particles in the fluid; and
    wherein said prism has a single optical entry face that is configured as a spherical surface centered at said point so that light enters the prism at a substantially perpendicular angle.

16. An optical assembly that measures fluid flowing through a pipeline, comprising:
    a light source that produces light focused at a point in the fluid;
    a prism located in the fluid that collects light scattered from particles in the fluid; and
    wherein said prism comprises a pentaprism with two internal reflecting surfaces and an entry surface configured so that light enters the pentaprism at a substantially perpendicular angle.

17. An optical assembly for focusing light from a fixed point in space within a light transparent fluid that may be of any refractive index, to a light receiver, comprising:
    a prism that is located in the fluid and which is constructed of a solid optical material with a single optical entry face that is configured as a spherical surface by a sphere centered about said point; and wherein the optical path from said optical entry surface of said prism to said light receiver comprises only solid optical material.

18. An optical assembly as in claim 17, wherein said light receiver couples to said prism via an optical fiber that attaches to said prism.

19. An optical assembly as in claim 17, wherein said prism includes at least one internal mirror that is forced by rotation of an ellipse about its major axis.

20. An optical assembly as in claim 17, wherein said prism includes at least one internal mirror that is a fabricated diffractive surface.

21. An optical assembly as in claim 17, wherein said prism comprises a right angle prism.

22. An optical assembly as in claim 17, wherein said prism comprises a pentaprism.

23. An optical assembly as in claim 22, wherein said prism further comprises a base surface to which said optical fiber attaches.

24. An optical assembly as in claim 22, wherein said prism includes an internal mirror that receives light through said entry face from said fixed point and reflects light to a second internal mirror that reflects light to said light receiver.

25. An optical assembly as in claim 24, wherein said pentaprism has 3 adjacent internal angles measuring 112.5°, 90°, and 112.5°.

26. An optical assembly as in claim 17, wherein said light receiver measures light scattered by particles suspended in the flow and the timing of the optical signal is used to measure the fluid velocity at said point.

27. An optical assembly as in claim 17, wherein said fluid is natural gas.

28. An optical assembly as in claim 19, wherein said light source illuminates particles suspended in the flow and the timing of the optical signal generated by light scattered by said particles is used to measure the fluid velocity at said point.

29. An optical assembly as in claim 20, wherein said light source illuminates particles suspended in the flow and the timing of the optical signal generated by light scattered by said particles is used to measure the fluid velocity at said point.

30. An optical flow meter for measuring fluid flow in a pressurized pipe, said flow meter comprising:
    a light source;
    a fiber optic coupled to said light source;
    a prism coupled to said fiber optic, said prism including:
        an entry surface through which light enters from the fiber optic;
        a first internal reflective surface that reflects the light received from said fiber optic;
        a second internal reflective surface, said second internal reflective surface focusing the reflected light from said first internal reflective surface to a point within the pressurized pipe; and
        an exit surface configured so that the light exits at a substantially perpendicular angle; and
    a collection lens that receives light scattered by particles in said fluid.

31. An optical flow meter as in claim 30, wherein said fiber optic attaches to said entry surface to prevent contaminants from blocking light emitted by said fiber optic.

32. An optical flow meter as in claim 30, wherein said first internal reflective surface comprises a flat mirrored surface.

33. An optical flow meter as in claim 30, wherein said second internal reflective surface comprises an elliptical mirrored surface.

34. An optical flow meter as in claim 33, wherein said elliptical mirrored surface is formed by rotation of an ellipse about its major axis.

35. An optical flow meter as in claim 30, wherein said second internal reflective surface comprises a diffractive surface.

36. An optical flow meter as in claim 30, wherein said prism comprises a pentaprism.

37. An optical flow meter as in claim 30, wherein said prism is mounted within the pressurized pipe environment.

38. An optical flow meter as in claim 30, wherein said prism is immersed in the fluid in said pressurized pipe.

39. A flow meter as in claim 30, wherein said prism may be used to measure the flow rate of fluids that have a different index of refraction.

40. A flow meter as in claim 30, further comprising a second prism, with a second fiber optic coupling said second prism to said light source.

41. A flow meter as in claim 40, wherein said prisms are integrally stacked.

42. A flow meter as in claim 30, wherein said collection lens comprises a prism.

43. A flow meter as in claim 42, further comprising a second fiber optic cable that couples said collection lens prism to a photo detector.

44. A flow meter as in claim 43, wherein said collection lens prism includes:
    an entry surface through which light enters from fixed point within the pressurized pipe, said entry surface having a spherical concave configuration with a radius centered substantially at said fixed point;
    a first internal reflective surface, said first internal reflective surface focusing the reflected light from said fixed point;
    a second internal reflective surface that reflects the light received from a first internal reflective surface; and
    an exit surface; and
        wherein said second fiber optic attaches to said exit surface to receive light from said prism.

45. A flow meter as in claim 30, wherein said exit surface has a spherical concave configuration with a radius centered substantially at said point within the pressurized pipe.

46. An optical flow meter for measuring fluid flow in a pressurized pipe, said flow meter comprising:
    a light source;
    a fiber optic coupled to said light source;
    an optical delivery system coupled to said fiber optic, said optical delivery system producing one or more light beams focused at a fixed point in said pressurized pipe; and
    a collection system that receives light scattered by particles in said fluid, said collection system including a prism, said prism including:
        an entry surface through which light enters from said fixed point within the pressurized pipe, said entry surface having a spherical concave configuration with a radius centered substantially at said fixed point;
        a first internal reflective surface, said first internal reflective surface focusing the reflected light from said fixed point;
        a second internal reflective surface that reflects the light received from a first internal reflective surface; and
        an exit surface; and
    a fiber optic that couples to said exit surface to receive light from said prism.

47. An optical flow meter as in claim 46, wherein said fiber optic attaches to said exit surface to prevent contaminants from blocking light emitted from said prism.

48. An optical flow meter as in claim 46, wherein said second internal reflective surface comprises a flat mirrored surface.

49. An optical flow meter as in claim 46, wherein said first internal reflective surface comprises an elliptical mirrored surface.

50. An optical flow meter as in claim 49, wherein said elliptical mirrored surface is formed by rotation of an ellipse about its major axis.

51. An optical flow meter as in claim 46, wherein said first internal reflective surface comprises a diffractive surface.

52. An optical flow meter as in claim 46, wherein said prism comprises a pentaprism.

53. An optical flow meter as in claim 46, wherein said prism is mounted within the pressurized pipe environment.

54. An optical flow meter as in claim 46, wherein said prism is immersed in the fluid in said pressurized pipe.

55. A flow meter as in claim 46, wherein said fiber optic couples said prism to a photo detector that may be used to measure the flow rate of fluids within the pressurized pipe, regardless of the index of refraction of the fluid.

56. A flow meter as in claim 55, wherein said collection system includes a second prism, with a second fiber optic coupling said second prism to said photo detector.

57. A flow meter as in claim 56, wherein said prisms are integrally stacked.

58. A flow meter as in claim 46, wherein said optical delivery system includes a prism.

* * * * *